(12) United States Patent
Kaveri et al.

(10) Patent No.: US 7,507,540 B1
(45) Date of Patent: Mar. 24, 2009

(54) CATALYTIC ANTI-FACTOR VIII ALLO-ANTIBODIES

(75) Inventors: Srinivas Kaveri, Malakoff (FR); Sébastien Lacroix-Desmazes, Ville D'Avray (FR); Michel Kazatchkine, Paris (FR)

(73) Assignees: Institut National de la Sante et de la Recherche Medicale (INSERM), Paris (FR); Bayer Pharma, Puteaux (FR)

( * ) Notice: Subject to any disclaimer, the term of this patent is extended or adjusted under 35 U.S.C. 154(b) by 577 days.

(21) Appl. No.: 10/031,938

(22) PCT Filed: Jul. 18, 2000

(86) PCT No.: PCT/EP00/06870

§ 371 (c)(1),
(2), (4) Date: Jul. 22, 2002

(87) PCT Pub. No.: WO01/07918

PCT Pub. Date: Feb. 1, 2001

(30) Foreign Application Priority Data

Jul. 21, 1999 (EP) .................................. 99401841

(51) Int. Cl.
G01N 33/53 (2006.01)
C12P 21/04 (2006.01)
A61K 35/14 (2006.01)
C12N 5/06 (2006.01)
C12N 9/00 (2006.01)

(52) U.S. Cl. .................. 435/7.1; 435/69.6; 435/7.7; 435/325; 435/326; 435/188.5; 530/383

(58) Field of Classification Search ................. 435/13, 435/188.5; 530/329
See application file for complete search history.

(56) References Cited

U.S. PATENT DOCUMENTS 5,744,326 A * 4/1998 Ill et al. ................. 435/69.1
5,744,446 A * 4/1998 Lollar et al. ............. 514/12
5,869,292 A * 2/1999 Voorberg ................. 435/69.6

OTHER PUBLICATIONS

Fulacher, C.A., et al. (1985) Proc. Natl. Acad. Sci., USA 82, 7728-7732.*
Giles, J.G.G., et al. (1993) Blood 82(8), 2452-2461.*
Fijnvandrast, K., et al. (1998) Blood 91(7), 2347-2352.*
Saenko, E.L., et al. (1994) J. Biol. Chem. 269(15), 11601-11605.*
Saenko, E.L., et al. (1996) J. Biol. Chem. 271(44), 27424-27431.*
Goldsmith, J.C. (1996) Blood Coagulation and Fibrinolysis 7(suppl), S3-S6.*

* cited by examiner

Primary Examiner—Rebecca E Prouty
Assistant Examiner—Md. Younus Meah
(74) Attorney, Agent, or Firm—Clark & Brody

(57) ABSTRACT

A method is disclosed of determining the presence of catalytic anti-Factor VIII allo-antibodies capable of degrading Factor VIII in a mammal, and of characterising the cleavage sites in said Factor VIII molecule by said catalytic anti-Factor VIII allo-antibodies. It also relates to an anti-Factor VIII allo-antibody-catalysed Factor VIII degradation inhibitor; and to a pharmaceutical composition comprising said catalytic anti-Factor VIII allo-antibodies which are capable of degrading Factor VIII and which originate from said method of determination; and further to a pharmaceutical composition comprising said anti-Factor VIII allo-antibody-catalysed Factor VIII degradation inhibitor. Finally, the present invention relates to the application in therapeutics of said anti-Factor VIII allo-antibody-catalysed Factor VIII degradation inhibitor, of a pharmaceutical composition comprising said catalytic anti-Factor VIII allo-antibodies which are capable of degrading Factor VIII and which originate from said method of determination, and of a pharmaceutical composition comprising said anti-Factor VIII allo-antibody-catalysed Factor VIII degradation inhibitor.

25 Claims, 5 Drawing Sheets

| $K_m$ (μM) | 9.46 ± 5.62 |
| --- | --- |
| $V_{Max}$ (fmoles/min) | 85.1 ± 60.1 |
| Catalytic constant (min$^{-1}$) | 0.026 ± 0.018 |
| Catalytic efficiency (M.min)$^{-1}$ | 2553 ± 533 |

CATALYTIC ANTI-FACTOR VIII ALLO-ANTIBODIES

FIELD OF THE INVENTION

The present invention relates to a method of determining the presence of catalytic anti-Factor VIII allo-antibodies capable of degrading Factor VIII in a mammal, and of characterising the cleavage sites in said Factor VIII molecule by said catalytic anti-Factor VIII allo-antibodies.

The present invention also relates to an anti-Factor VIII allo-antibody-catalysed Factor VIII degradation inhibitor.

The present invention further relates to a pharmaceutical composition comprising said catalytic anti-Factor VIII allo-antibodies which are capable of degrading Factor VIII and which originate from said method of determination, and to a pharmaceutical composition comprising said anti-Factor VIII allo-antibody-catalysed Factor VIII degradation inhibitor.

Finally, the present invention relates to the application in therapeutics of said anti-Factor VIII allo-antibody-catalysed Factor VIII degradation inhibitor, of a pharmaceutical composition comprising said catalytic anti-Factor VIII allo-antibodies which are capable of degrading Factor VIII and which originate from said method of determination, and of a pharmaceutical composition comprising said anti-Factor VIII allo-antibody-catalysed Factor VIII degradation inhibitor.

BACKGROUND TO THE INVENTION

Haemophilia A is an X chromosome-linked recessive disorder resulting in defective or deficient Factor VIII molecules, which, in its severe form, is a life-threatening and crippling haemorrhagic disease.

Infusion of homologous Factor VIII to patients with severe haemophilia A results, in 25% of the cases, in the emergence of anti-Factor VIII allo-antibodies (Ehrenforth, S., Kreuz, W., Scharrer, I., Linde, R., Funk, M., Güngör, T., Krackhardt, B. and Komhuber, B., (<<*Incidence of development of factor VIII and factor IX inhibitors in haemophiliacs*>>, Lancet, 1992, 339: 594-598), that inhibit Factor VIII procoagulant activity by steric hindrance of the interaction of Factor VIII either with stabilising molecules (Saenko, E. L., Shima, M., Rajalakshmi, K. J. and Scandella, D., <<*A role for the C2 domain of factor VIII in binding to von Willebrand factor*>>, J. Biol. Chem., 1994, 269: 11601-11605; and Saenko, E. L., Shima, M., Gilbert, G. E., and Scandella, D., <<*Slowed release of thrombin-cleaved factor VIII from von Willebrand factor by a monoclonal and a human antibody is a novel mechanism for factor VIII inhibition*>>, J. Biol. Chem., 1996, 271: 27424-27431), with molecules essential for its activity (Arai, M., Scandella, D., and Hoyer, L. W., <21 *Molecular basis of factor VIII inhibition by human antibodies: Antibodies that bind to the factor VIII light chain prevent the interaction of factor VIII with phospholipid*>>, J. Clin. Invest., 1989, 83:1978-1984; and Zhong, D., Saenko, E. L., Shima, M., Felch, M. and Scandella, D., <<*Some human inhibitor antibodies interfere with factor VIII binding to Factor IX*>>, Blood, 1998, 92: 136-142), or with activating molecules (Lubahn, B. C., Ware, J., Stafford, D. W., and Reiser, H. M., <<*Identification of a FVIII epitope recognized by a human hemophilic inhibitor*>>, Blood, 1989, 73: 497-499; and Neuenschwander, P. F., and Jesty, J., <<*Thrombin-activated and factor Xa-activated human factor VIII: differences in cofactor activity and decay rate*>>, Arc. Biochem. Biophys., 1992, 296: 426-434).

SUMMARY OF THE INVENTION

In an entirely surprising way, a discovery has been made by the Applicants of a degradation of Factor VIII by allo-antibodies of two high responder patients with severe haemophilia A, demonstrating a heretofore unknown mechanism by which Factor VIII inhibitors may prevent the pro-coagulant function of Factor VIII.

The Applicant's discovery of catalytic anti-Factor VIII allo-antibodies is to the best of his knowledge the first report on the emergence of catalytic antibodies that are INDUCED upon treatment of patients with Factor VIII. It was heretofore considered very surprising, even absurd or unbelievable, that antibodies are formed, in the presence of Factor VIII, which would actually render the Factor VIII molecule inactive through catalytic hydrolysis (<<proteolysis >>). However, the catalytic antibodies reported so far, are all auto-antibodies found in the course of a disease process or in physiological conditions. Thus, induced antibodies are called ALLO-antibodies, the origin of which is clearly different from the origin of AUTO-antibodies in any auto-immune disease.

The calculated average Km and apparent Vmax for the reaction of anti-Factor VIII antibodies of one of the patients were $9.46\pm5.62$ μM and $85\pm60$ fmol.min$^{-1}$, respectively. The kinetic parameters of Factor VIII hydrolysis suggest a functional role for the catalytic immune response in the inactivation of Factor VIII in vivo.

The characterisation of anti-Factor VIII allo-antibodies as site-specific proteases hence provide new approaches to the treatment of diseases of a patient who possess anti-Factor VIII allo-antibodies.

Thus, according to a first aspect, the present invention provides a method of determining the presence of catalytic anti-Factor VIII allo-antibodies capable of degrading Factor VIII in a mammal, characterised in that it comprises:
i) isolating the plasma from a sample of blood taken from said mammal,
ii) isolating anti-Factor VIII allo-antibodies from said plasma;
iii) placing said anti-Factor VIII allo-antibodies in contact with Factor VIII for a period of time sufficient to permit any degradation of said Factor VIII by said anti-Factor VIII allo-antibodies; and
iv) determining, after said period of time, whether said Factor VIII has effectively been degraded by said anti-Factor VIII allo-antibodies.

According to an embodiment of step ii) of the method of the present invention, said anti-Factor VIII allo-antibodies are isolated from said plasma by combining them with said Factor VIII, said Factor VIII being preferably coupled to a matrix. Advantageously, in step ii), said anti-Factor VIII allo-antibodies are isolated by affinity chromatography. Preferably, in step ii), said affinity chromatography comprises the use of a Sepharose matrix, preferably activated with cyanogen bromide.

According to an embodiment of step iii) of the method of the present invention, said Factor VIII is labelled with a labelling agent, preferably a radio-labelling agent, such as $^{125}$I in particular. Advantageously, in step iii), said Factor VIII is placed in contact with the anti-Factor VIII allo-antibodies for a period of time of between about 0.5 and about 30 hours, preferably about 10 hours, at a temperature of about 15 to about 40° C., preferably 38° C.

According to an embodiment of step iv) of the method of the present invention, the determination of whether said Factor VIII has effectively been degraded by said anti-Factor VIII allo-antibodies is carried out by a determination comprising a separation technique, such as gel electrophoresis, such as SDS PAGE in particular, or gel filtration, such as fast protein liquid chromatography gel filtration in particular, and a visualisation technique, such as autoradiography in particular.

In accordance with a further embodiment of the method of the present invention, said method is characterised in that it further comprises:

v) characterising the site(s) in said Factor VIII molecule cleaved by said anti-Factor VIII allo-antibodies.

According to an embodiment of step v) of the method of the present invention, said characterisation is carried out by placing said Factor VIII in contact with said anti-Factor VIII allo-antibodies capable of degrading Factor VIII, separating and then sequencing the fragments of Factor VIII resulting therefrom. Advantageously, said separation is carried out using a technique such as gel electrophoresis, such as SDS PAGE in particular, or gel filtration. Said sequencing is advantageously carried out using a technique such as N-terminal sequencing, such as by using an automatic protein microsequencer in particular. By using the said sequencing, the following scissile bonds are located: $Arg^{372}$-$Ser^{373}$, located between the A1 and A2 domains, $Tyr^{1680}$-$Asp^{1681}$, located on the N-terminus of the A3 domain, and $Glu^{1794}$-$Asp^{1795}$ located within the A3 domain of the Factor VIII molecule.

According to a second aspect, therefore, the present invention provides an amino acid sequence:

Ser Val Ala Lys Lys His Pro (SEQ ID NO: 1);

an amino acid sequence:

Asp Glu Asp Glu Asn Gln Ser (SEQ ID NO: 2); and an amino acid sequence:

Asp Gln Arg Gln Gly Ala Glu (SEQ ID NO: 3).

The present invention also extends to variants or analogues of this or any other sequence of Factor VIII which are capable of inhibiting any site in the Factor VIII molecule which is susceptible to being lysed by an anti-Factor VIII allo-antibody. Within the context of the present invention, such a variant can be, for example, a peptide or non-peptide analogue of an amino acid sequence described supra which inhibits any site in the Factor VIII molecule which is susceptible to being lysed by an anti-Factor VIII allo-antibody. Such a variant can be, for example, a variant of the sequence which is either shorter by a few amino acids, at the N-terminal, the C-terminal, or both termini, for example, or longer by a few amino acids (it being possible to obtain such variants by chemical synthesis or by enzymatic digestion of the naturally occurring molecule), so long as the variant inhibits any site in the Factor VIII molecule which is susceptible to being lysed by an anti-Factor VIII allo-antibody.

Hence, according to a third aspect, the present invention provides an anti-Factor VIII allo-antibody-catalysed Factor VIII degradation inhibitor. Advantageously, this inhibitor is characterized in that it comprises a protease inhibitor. Examples of protease inhibitors that can be used as anti-Factor VIII allo-antibody-catalysed Factor VIII degradation inhibitors within the context of the present invention, without being limited thereto, are fluorophosphate-type inhibitors, such as DFP for example, or sulphonyl fluoride-type inhibitors, such as PMSF or AEBSF (4-(2-aminoethyl)benzene-sulphonyl fluoride hydrochloride (notably marketed by Roche Diagnostics GmbH, Mannheim, Germany, under the trademark Pefabloc®)), for example. More particularly, this inhibitor is characterized in that said inhibitor inhibits cleavage of the scissile bonds: $Arg^{372}$-$Ser^{373}$, located between the A1 domains, $Tyr^{1680}$-$Asp^{1681}$, located on the N-terminus of the A3 domain, and $Glu^{1794}$-$Asp^{1795}$ located within the A3 domain of the Factor VIII molecule. More preferably still, this inhibitor is characterized in that it comprises a peptide or non-peptide analogue of the amino acid sequence:

Ser Val Ala Lys Lys His Pro (SEQ ID NO: 1);

a peptide or non-peptide analogue of the amino acid sequence:

Asp Glu Asp Glu Asn Gln Ser (SEQ ID NO: 2); or a peptide or non-peptide analogue of the amino acid sequence:

Asp Gln Arg Gln Gly Ala Glu (SEQ ID NO: 3).

The Factor VIII degradation inhibitors as defined supra, as well as their addition salts, in particular their pharmaceutically acceptable addition salts, have a very valuable pharmacological profile in that they possess neutralizing activity towards anti-Factor VIII allo-antibodies.

These properties justify their application in therapeutics and the invention further relates, by way of drugs, to the Factor VIII degradation inhibitors above, as well as their addition salts, in particular their pharmaceutically acceptable addition salts.

They will therefore be particularly indicated in the treatment of diseases of, inter alia, haemophilic nature, more particularly diseases involving coagulation defects due to Factor VIII insufficiency.

An example of their use which may be mentioned is the treatment of high responder patients with diseases such as mild or severe haemophilia A, for example (in the case in which catalytic antibodies are found in these patients), on the one hand, and/or, on the other hand, patients suffering from auto-immune diseases for example (in the case in which catalytic antibodies are found in these patients).

Thus, according to a fourth principal aspect, the present invention provides a solution to a long-felt need through a pharmaceutical composition characterised in that it comprises a pharmaceutically effective amount of at least one anti-Factor VIII allo-antibody capable of degrading Factor VIII, as defined supra, notably as obtainable from the method described supra, or one of its pharmaceutically acceptable addition salts incorporated in a pharmaceutically acceptable excipient, vehicle or carrier.

Further, according to a fifth principal aspect, the present invention provides a pharmaceutical composition characterised in that it comprises a pharmaceutically effective amount of at least one Factor VIII degradation inhibitor, as defined supra, or one of its pharmaceutically acceptable addition salts incorporated in a pharmaceutically acceptable excipient, vehicle or carrier.

These compositions can be administered by the buccal, rectal, parenteral, transdermal, ocular, nasal or auricular route, for example.

These compositions can be solid or liquid and can be presented in the pharmaceutical forms commonly used in human medicine, such as, for example, simple or coated tablets, gelatine capsules, granules, suppositories, injectable preparations, transdermal systems, eye drops, aerosols and sprays, and ear drops. They are prepared by the customary methods. The active principle, which consists of a pharmaceutically effective amount of at least one Factor VIII degradation inhibitor as defined supra, or one of its pharmaceutically acceptable addition salts can be incorporated therein together with excipients normally employed in pharmaceutical compositions, such as talc, gum Arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colours. The preferred pharmaceutical form is an injectable form.

The invention also covers a pharmaceutical composition with neutralising activity which can be used especially as a favourable treatment of diseases such as haemophilia A with production of anti-Factor VIII allo-antibodies; autoimmune diseases with anti-Factor VIII allo-antibodies (in case catalytic antibodies are found in these patients) in particular, said composition being characterised in that it comprises a pharmaceutically effective amount of at least one Factor VIII degradation inhibitor above, or one of its pharmaceutically acceptable addition salts incorporated in a pharmaceutically acceptable excipient, vehicle or carrier.

The invention also covers a method of therapeutic treatment of a mammal suffering from a pathology resulting from the level of Factor VIII in the blood thereof, characterised in that a therapeutically effective amount of at least one Factor VIII degradation inhibitor as defined supra or one of its pharmaceutically acceptable addition salts is administered to the said mammal.

This method affords especially a favourable treatment of diseases of haemophilic nature, in particular a pathology resulting from a lack of Factor VIII in the blood thereof.

The invention also covers a pharmaceutical composition with anti-thrombotic activity which can be used especially as a favourable treatment of diseases such as thrombosis in particular, said composition being characterised in that it comprises a pharmaceutically effective amount of at least one anti-Factor VIII allo-antibody capable of degrading Factor VIII, notably as obtainable from the method described above, or one of its pharmaceutically acceptable addition salts incorporated in a pharmaceutically acceptable excipient, vehicle or carrier.

The invention also covers a method of therapeutic treatment of mammals, characterised in that a therapeutically effective amount of at least one anti-Factor VIII allo-antibody as defined supra or one of its pharmaceutically acceptable addition salts is administered to the said mammal.

This method affords especially a favourable treatment of diseases of thrombotic nature, in particular said pathology resulting from the presence of an excess of Factor VIII in the blood thereof.

In human and animal therapeutics, the anti-Factor VIII allo-antibodies or the Factor VIII degradation inhibitors as defined supra can be administered by themselves or in association with a physiologically acceptable excipient, in any form, in particular orally in the form of gelatine capsules or tablets, or parenterally in the form of injectable solutions. It is possible to envisage other forms of administration such as suppositories, ointments, creams, gels or aerosol preparations.

Within the context of the present invention, the following terms are used:

<<catalytic anti-Factor VIII allo-antibodies >>, which is understood as meaning antibodies directed to Factor VIII endowed with a catalytic activity induced in haemophilia A patients upon transfusion with therapeutic preparations of Factor VIII;

<<Factor VIII>>, which is understood as meaning a co-enzyme of Factor IX in the enzymatic cleavage of Factor X during the blood coagulation process;

<<degradation of Factor VIII>>, which is understood as meaning the generation of fragments from Factor VIII that do not appear due to a spontaneous hydrolysis, or due to hydrolysis by physiologically cleaving enzymes, i.e. thrombin, activated Factor IX, activated Factor X, and activated protein C;

<<anti-Factor VIII allo-antibody-catalysed Factor VIII degradation inhibitor>>, which is understood as meaning any peptide, belonging or not to the Factor VIII sequence, or protease inhibitor that are capable of specifically neutralising the hydrolysing activity of anti-Factor VIII catalytic antibodies;

DESCRIPTION OF A PREFERRED EMBODIMENT OF THE PRESENT INVENTION

Human recombinant Factor VIII was radio-labelled with $^{125}$I. Anti-Factor VIII allo-antibodies were affinity-purified from the plasma of three haemophilia patients with inhibitor on a Sepharose matrix to which immunopurified human Factor VIII had been coupled. Affinity-purified anti-Factor VIII antibodies of patients Bor, Che and Wal inhibited Factor VIII pro-coagulant activity up to 57.0, 64.0 and 43.0 BU/mg of IgG, respectively.

Co-incubation of labelled Factor VIII with the anti-Factor VIII allo-antibodies resulted, in the case of two patients out of three, in the proteolysis of the molecule. The specificity of the hydrolysis on the antibody combining sites of anti-Factor VIII allo-antibodies of the IgG isotype was demonstrated. Co-incubation of [$^{125}$I]-Factor VIII with affinity-purified anti-Factor VIII IgG of patients Bor and Wal in the presence of the protease inhibitors aprotinin (0.15 µM), E-64 (28 µM), EDTA (1.3 µM), leupeptin (10 µM), and pepstatin (10 µM) did not result in inhibition of proteolytic activity.

The Applicants have characterised the major cleavage sites for catalytic IgG in the Factor VIII molecule, to be as follows: $Arg^{372}$-$Ser^{373}$, located between the A1 and A2 domains of Factor VIII; $Tyr^{1680}$-$Asp^{1681}$, located on the N-terminus of the A3 domain; and $Glu^{1794}$-$Asp^{1795}$ located within the A3 domain.

The time and dose-dependency of the hydrolysis of Factor VIII by anti-Factor vm allo-antibodies has been demonstrated. In particular, hydrolysis was observed under conditions where anti-Factor VIII IgG and Factor VIII were co-incubated at molar ratios that were 80- to 9500-fold lower than those expected to be present in patients' plasma, suggesting that hydrolysis is a mechanism of Factor VIII inactivation by the patients' allo-antibodies in vivo.

The Applicants have further investigated the kinetics of antibody-mediated hydrolysis of Factor VIII by incubating anti-Factor VIII IgG of patient Wal with increasing concentrations of unlabeled Factor VIII in the presence of a fixed concentration of [$^{125}$I]-Factor VIII. The curves of the reciprocal of the velocity plotted as a function of the reciprocal of the substrate concentration were linear (r=0.99), suggesting that the reaction conformed to simple Michaelis-Menten kinetics, as already observed for polyclonal catalytic autoantibodies. The apparent catalytic efficiency, Vmax and rate of hydrolysis of anti-Factor VIII allo-antibodies were calculated in the case of patient Wal. The kinetic parameters of hydrolysis calculated in vitro, suggest that proteolysis may be a mechanism of Factor VM inactivation by patients' alloantibodies in vivo.

The association of Factor VIII with von Willebrand Factor (vWF) increases the catalytic rate of thrombin for Factor VIII, whereas it protects Factor VIII from hydrolysis by activated protein C (APC). The addition of vWF to Factor VIII resulted in partial inhibition of hydrolysis of Factor VIII by anti-Factor VIII IgG, i.e. 36.9%, when purified vWF and Factor VIII were mixed using a wt/wt ratio similar to that present in normal plasma, i.e. 30 µg/ml of vWF versus 300 ng/ml of Factor VIII.

The identification of anti-Factor VIII allo-antibodies as catalytic antibodies extends the spectrum of catalytic immune responses, in addition to previous reports of hydrolysing antibodies against vasoactive intestinal peptide (VIP) in asthma patients, DNA-hydrolysing antibodies in patients with SLE and thyroglobulin-specific catalytic antibodies in patients with autoimmune thyroiditis. This is also the first report to the knowledge of the Applicants of the induction of a catalytic antibody in the human, in response to exogeneous administration of a protein antigen. The kinetic parameters of Factor VIII hydrolysis by anti-Factor VIII IgG exhibiting catalytic properties and the estimated amounts of these antibodies in plasma, suggest a functional role for the catalytic immune response in inactivating Factor VIII in vivo. Within a polyclonal mixture of anti-Factor VIII allo-antibodies which differ in their functional properties, catalytic antibodies may inhibit Factor VIII pro-coagulant activity at faster rates than non-catalysing anti-Factor VIII antibodies. Identification of peptide epitopes that are the targets for proteolytic anti-Factor VIII antibodies may thus be critical for our understanding of the pathophysiology of the Factor VIII inhibitor response. Furthermore, the characterisation of Factor VIII inhibitors as site-specific proteases will provide new approaches to the treatment of patients possessing anti-Factor VIII allo-antibodies.

BRIEF DESCRIPTION OF THE FIGURES

The invention will be better understood and other objects, characteristics and advantages thereof will become more clearly apparent from the following explanatory description referring to the attached Figures, which are given solely by way of non-limiting Examples illustrating the specificity of the cleavage of Factor VIII by anti-Factor VIII allo-antibodies.

FIG. 1(A):

[125I]-labelled Factor VIII was incubated with affinity-purified anti-Factor VIII IgG of patients Bor (lane Bor), Che (lane Che) and Wal (lane Wal), or with buffer alone (lane 1) for 10 h at 38° C. prior to SDS-PAGE and autoradiography. In two of the three patients (Bor and Wal), incubation of Factor VIII with affinity-purified anti-Factor VIII IgG resulted in hydrolysis of the Factor VIII molecule. In contrast, the migration profile of Factor VIII was unchanged when [$^{125}$I]-labelled Factor VIII was incubated with anti-Factor VIII IgG purified from the plasma of patient Che (lane Che). The migration profile of Factor VIII was also unchanged upon incubation with human monoclonal M061 anti-digoxin IgG (mAb) or with normal unfractionated polyclonal human IgG (Sandoglobulin®, IVIg) that exhibit no inhibitory activity to Factor VIII.

FIG. 1(B):

Flow-throughs of the affinity columns were devoid of anti-Factor VIII antibodies as determined by ELISA, and did not hydrolyse [$^{125}$I]-labelled Factor VIII.

FIG. 1C:

Removal of IgG from the acid eluates containing affinity-purified anti-Factor VM antibodies of patients Wal and Bor by chromatography on protein G, resulted in the loss of their hydrolytic activity to Factor VIII.

Figure 1:
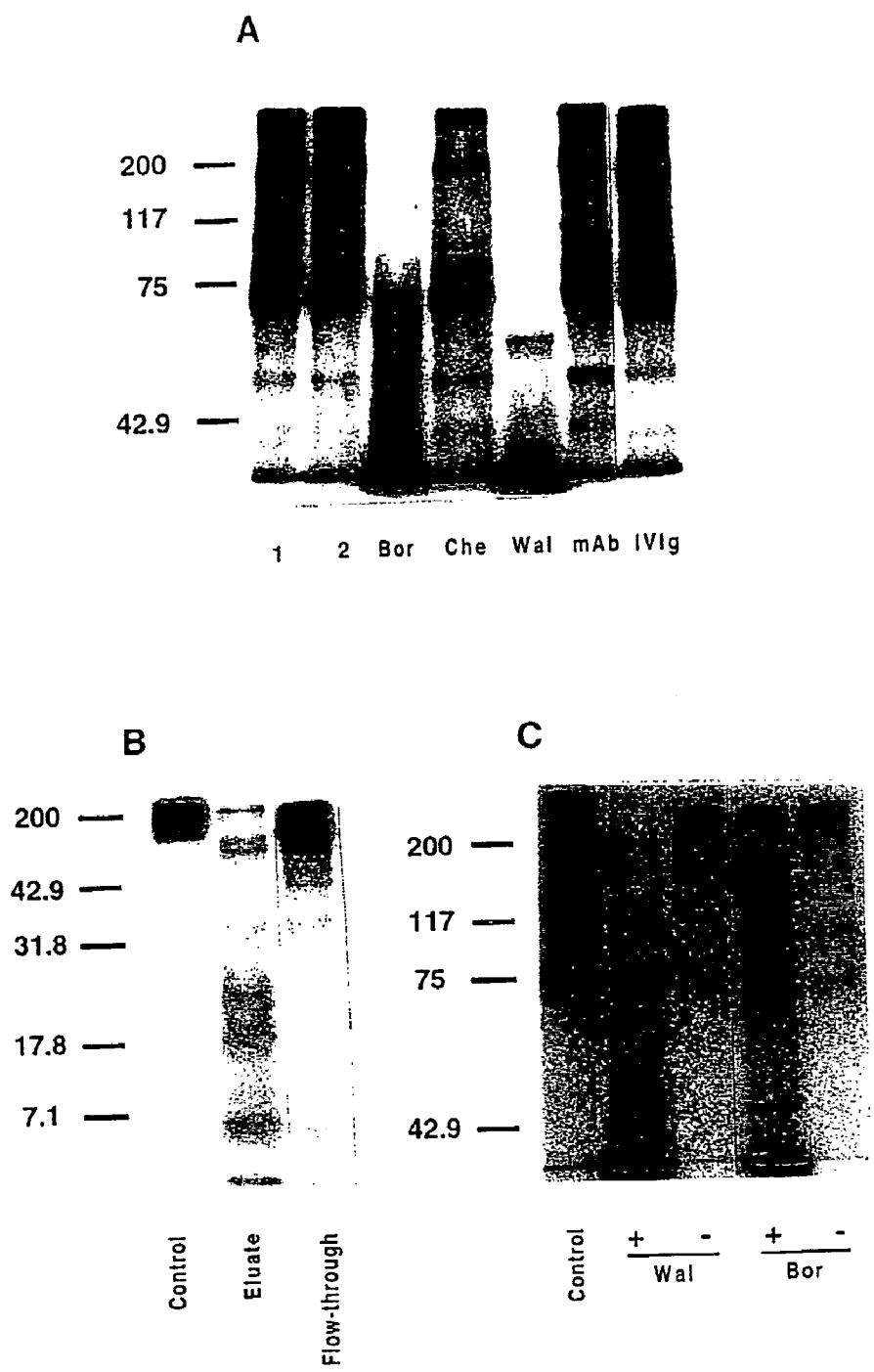
FIG. 1: Hydrolysis of [$^{125}$I]-Factor VIII by Affinity-Purified Anti-Factor VIII IgG Antibodies of Haemophilia A Patients with Inhibitor
Figure 2:
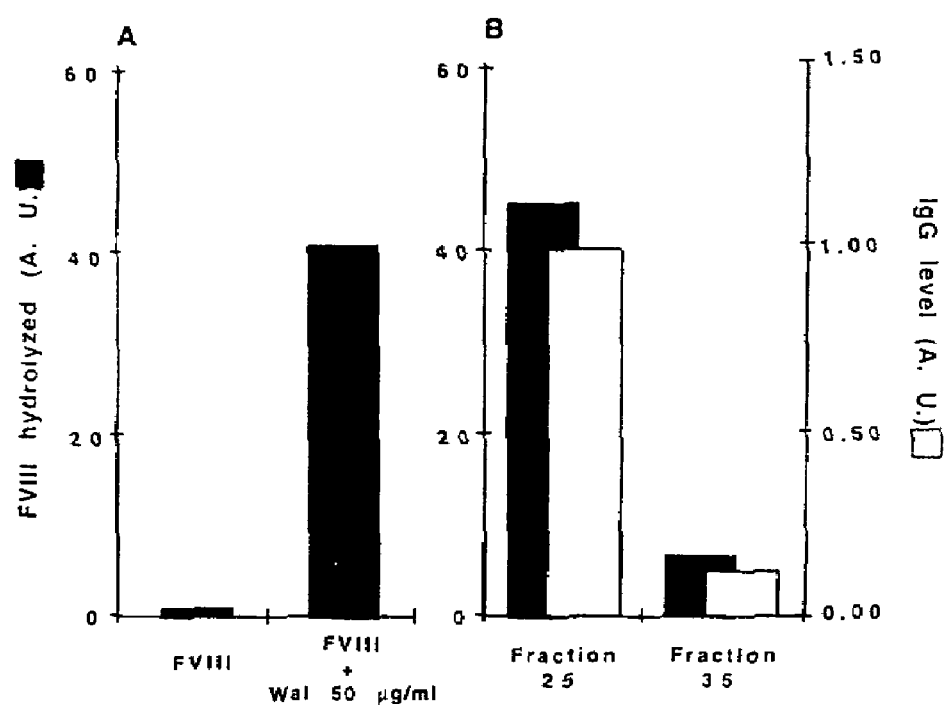

FIG. 2: Size Exclusion Chromatography of the Catalytic Activity of Anti-Factor VIII Antibodies

FIG. 2(A):

To further exclude the possibility that the proteolytic activity of the antibodies was due to contaminating proteases, affinity-purified anti-Factor VIII antibodies of patient Wal were treated with 8 M urea and subjected to size exclusion chromatography. A major peak was isolated in fraction 25 that corresponded to IgG as indicated by ELISA. The hydrolysing activity co-eluted with the IgG fraction and that the activity was not detected in fractions in which IgG was not present (e.g., fraction 35).

FIG. 2(B):

The major peak that was isolated in fraction 25 corresponded to IgG as indicated by SDS-PAGE of the radiolabelled content of the fraction.

FIGS. 3A-D: Dose- and time-dependency of proteolysis of [$^{125}$I]-Factor VIII by affinity-purified anti-Factor VIII antibodies of haemophilia A patients with inhibitor.

Figure 3:
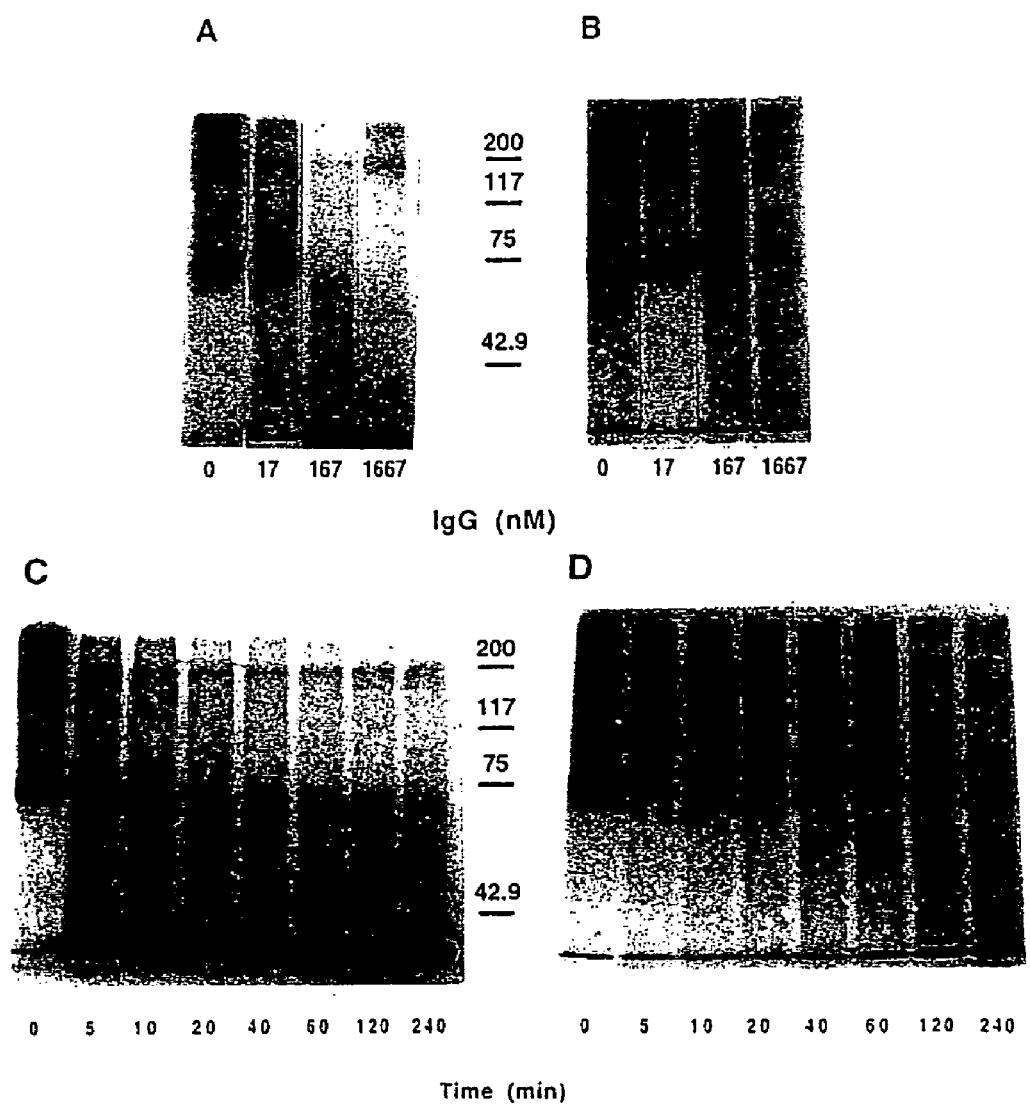

The kinetics of the hydrolysis of Factor VIII by anti-Factor VIII allo-antibodies of patients Bor (FIGS. 3A and 3C) and Wal (FIGS. 3B and 3D). The rate of hydrolysis of [I-125-]-labelled Factor VIII by anti-Factor IgG of patient Wal was faster than that exhibited by anti-Factor VIII IgG of patient Bor, suggesting either that catalytic antibodies of the patients exhibit different kinetic properties, or, alternatively, that the proportion of catalytic antibodies among the anti-Factor VIII antibodies differ between the patients.

Figure 4:
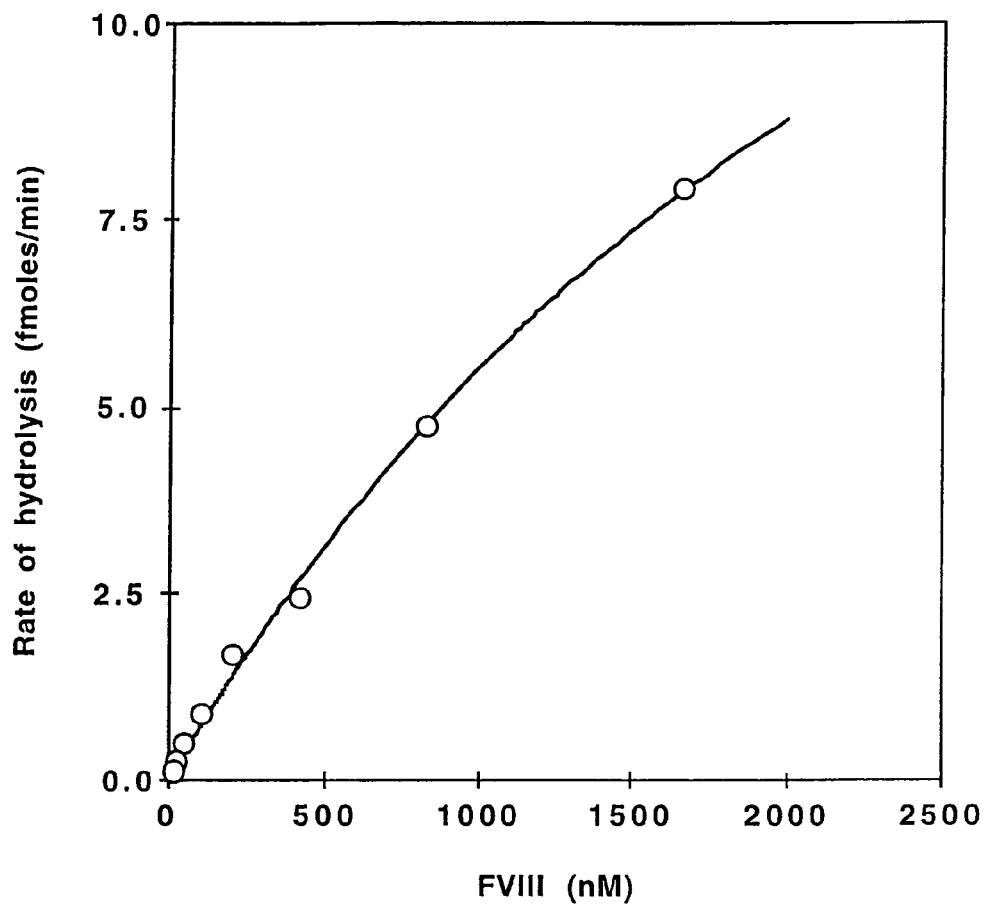

FIG. 4: Hydrolysis of [$^{125}$I]-Factor VIII by Anti-Factor VIII IgG Antibodies in the Presence of Increasing Amounts of Cold Factor VIII Kinetics of antibody-mediated hydrolysis of Factor VIII by incubating anti-Factor VIII IgG of patient Wal with increasing concentrations of unlabelled Factor VIII in the presence of a fixed concentration of [$^{125}$I]-Factor VIII. The addition of increasing amounts of unlabelled Factor VIII resulted in dose-dependent inhibition of hydrolysis of [$^{125}$I]-Factor VIII by anti-Factor VIII IgG. Saturation of Factor vm hydrolysis was not attained with the maximum concentration of Factor VIII that was used (i.e. 1.7 µM). The curves of the reciprocal of the velocity plotted as a function of the reciprocal of the substrate concentration were linear (r=0.99), suggesting that the reaction conformed to simple Michaelis-Menten kinetics, as already observed for polyclonal catalytic auto-antibodies.

Figure 5:
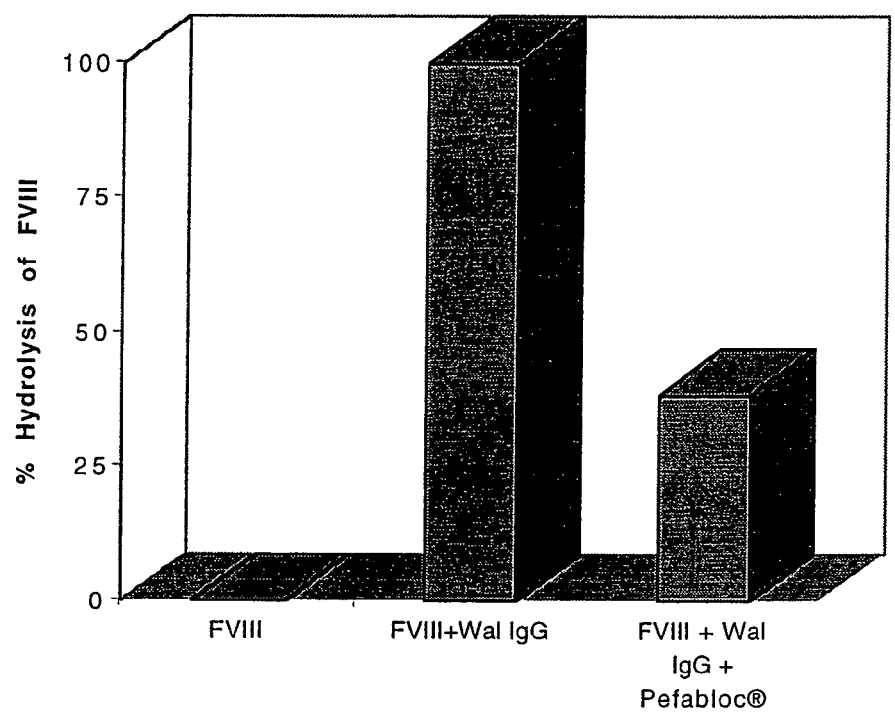

FIG. 5: Inhibition of Catalytic Activity of Anti-Factor VIII IgG of Patient Wal

The proteolysis of radio-labelled Factor VIII by the anti-Factor VIII allo-antibodies of patient Wal was inhibited to about 62% when the antibodies and Factor VIII were co-incubated in the presence of Pefabloc® (marketed by Roche Diagnostics GmbH, Mannheim, Germany), indicating the potency of certain serine protease inhibitor to neutralise the catalytic activity of some of the catalytic antibodies.

EXAMPLES

Example I

Affinity-Purification of Anti-Factor VIII Antibodies

Antibodies were isolated from plasma by ammonium sulphate precipitation. Antibodies reactive with Factor VIII were then affinity-purified on a CNBr-activated Sepharose 4B matrix to which immuno-purified commercial human plasma-derived Factor VIII had been coupled (25000 U/3 g of gel). The flow-throughs of the columns were collected. After extensive washing with PBS pH 7.4, anti-Factor VIII antibodies were eluted using 0.2 M glycine pH 2.8, dialysed against PBS and concentrated with Centriprep. Flow-throughs and eluates were aliquoted and stored at −20° C. until use. F(ab')$_2$ fragments of anti-Factor VIII antibodies were prepared as previously described.

The concentration of anti-Factor VIII IgG was 130, 20 and 280 µg per 10 mg of IgG applied to the column in the case of patients Bor, Che and Wal, respectively, (i.e., 143±130 µg/ml of unfractionated plasma), which is in agreement with previous observations.

Example II

Factor VIII-Neutralising Activity

The Factor VIII-neutralising activity of anti-Factor VIII antibodies was determined by the method of Kasper et al. and expressed as Bethesda units (BU) (ref). BU were defined as the inverse of the concentration of IgG which causes 50% inhibition of Factor VIII procoagulant activity. Residual Factor VIII activity was measured in a one-stage assay by determination of the activated partial thromboplastin time using human plasma depleted of Factor VIII (Behring) as substrate and human placental pathromtin® (Behring) as activators. Heated plasma or immunopurified anti-Factor Vm IgG to be tested, were incubated with pooled citrated human plasma for 2 h at 37° C. The clotting time of four serial dilutions of a reference plasma pool (Immuno AG, Wien) was compared with the clotting time of three dilutions of each sample to be tested. Dilutions were carried out in Owren-Koller buffer (Diagnostica Stago). Inter-assay variation ranged between 1 and 2.5%.

Affinity-purified anti-Factor VIII antibodies of patients Bor, Che and Wal inhibited Factor VIII pro-coagulant activity up to 57.0, 64.0 and 43.0 BU/mg of IgG, respectively.

Example III

Assay for Hydrolysis of Factor VIII

Commercial human recombinant Factor VIII was labelled with $^{125}$I to a specific activity of 11.6 nCi/µg, by using the iodogen method. [$^{125}$I]-Factor VIII (1.5 to 150 ng) was incubated in 50 µl of 50 mM tris-HCl pH 7.7, 100 mM glycine, 0.025% Tween-20 and 0.02% NaN$_3$ alone or with 17 to 1667 nM of immuno-purified anti-Factor VIII IgG for 5 min to 10 hours at 38° C. Human monoclonal anti-digoxin IgG M061 (mAb) and normal unfractionated human polyclonal IgG (IVIg, Sandoglobulin®), were used as negative controls. Samples were mixed 1:1 with Laemmli's buffer without mercaptoethanol, and were subjected to SDS electrophoresis without boiling, after loading 20 µl of each sample per lane. Samples were run in parallel on 7.5% and 15% SDS-PAGE under non-reducing conditions, after loading 20 µl of each sample per lane. Migration was performed at room temperature using a mini-PROTEAN II system at 25 mA/gel, until the dye front reached the bottom of the gel. The gels were then dried and protein bands revealed using X-OMAT AR. Following autoradiography, the Factor VIII bands of apparent molecular weight 200 and 300 kDa that are consistently hydrolysed by anti-Factor VIII IgG, were scanned so as to allow for the calculation of the rate of hydrolysis of labelled Factor VIII.

Example IV

Fast Protein Liquid Chromatography Gel Filtration

A hundred µl aliquot of anti-Factor VIII IgG of patient Wal (740 µg) treated with 8M urea was subjected to gel filtration on a superose-12 column equilibrated with PBS-0.01% azide at a flow rate of 0.2 ml/min. Five hundred µl fractions were collected and assayed for the presence of IgG by sandwich ELISA and for Factor VIII proteolytic activity after ten-fold dilution. The proteins in fraction 25 were radiolabelled with $^{125}$I and subjected to SDS-PAGE under non-reducing conditions in parallel with normal polyclonal human IgG. The gel was stained with Comassie Blue, and also autoradiographed; both images were then overlaid. A major peak was isolated in fraction 25 that corresponded to IgG as indicated by ELISA and SDS-PAGE of the radiolabelled content of the fraction. The hydrolysing activity co-eluted with the IgG fraction and that the activity was not detected in fractions in which IgG was not present (e.g., fraction 35).

Example V

Analysis of NH$_2$-Terminal Sequences

Unlabelled human recombinant Factor VIII sucrose formulation (rDNA-BHK) (300 µg, octocog alfa, Bayer Corporation, Berkeley, Calif.) was treated with the anti-Factor VIII IgG of patient Wal (74 µg) in 1500 µl of 50 mM tris-HCl pH 7.7, 100 mM glycine, 0.025% tween-20 and 0.02% NaN$_3$ for 24 hours at 38° C. The resultant Factor VM fragments were run on a 10% SDS-PAGE at 50 mA under non-reducing conditions and transferred for 2 hours at 100 mA on a Hybond-P PVDF membrane (Amersham, Little Chalfont, England) in 10 mM CAPS, 10% ethanol at pH 11.0. After staining with coomassie blue, visible bands were cut and subjected to N-terminal sequencing, using an automatic protein microsequencer Prosize 492 cLC (PE-Applied Biosystems, Foster City, Calif.). The amount of protein sequenced ranged from 0.5 to 2 pmoles, depending on the fragment.

The major scissile bonds were as follows: Arg$^{372}$-Ser$^{373}$ (R$^{372}$-S$^{373}$), located between the A1 and A2 domains of Factor VIII; Tyr$^{1680}$-Asp$^{1681}$ (Y$^{1680}$-D$^{1681}$), located in the N-terminus of the A3 domain; and Glu$^{1794}$-Asp$^{1795}$ (E$^{1794}$-D$^{1795}$) located within the A3 domain. Multiple site cleavage of Factor VIII by anti-Factor VIII antibodies might originate from individual antibodies with polyspecific catalytic activities or polyclonal populations of antibodies, each exhibiting a unique cleavage site specificity.

| Amino acid sequence | Cleavage site |
|---|---|
| Ser Val Ala Lys Lys His Pro (SVAKKHP) (SEQ ID NO: 1) | Arg$^{372}$ – Ser$^{373}$ (R$^{372}$ – S$^{373}$) |
| Asp Gln Arg Gln Gly Ala Glu (DQRQGAE) (SEQ ID NO: 3) | Glu1$^{794}$ – Asp$^{1795}$ (E$^{1794}$ – D$^{1795}$) |
| Asp Glu Asp Glu Asn Gln Ser (DEDENQS) (SEQ ID NO: 2) | Tyr$^{1680}$ – Asp$^{1681}$ (Y$^{1680}$ – D$^{1681}$) |

Example VI

Inhibition Studies were Performed using Pefabloc®, a Generic Inhibitor of Serine Proteases Hydrolysis of [$^{125}$I]-Factor VIII by affinity-purified anti-Factor VIII IgG antibodies of haemophilia A patients with inhibitor in the presence of Pefabloc®. [$^{125}$I]-Factor VIII (150 ng) was incubated alone, with 50 µg/ml of immunopurified anti-Factor VIII IgG of patient Wal or in the presence of both anti-Factor VIII IgG and 4 mM of the serine protease inhibitor Pefabloc® (Boehringer) for 5 h at 38° C. Factor VIII was then analysed by 7.5% SDS-PAGE under non-reducing conditions. Following autoradiography, the Factor VIII bands of apparent molecular weight 200 and 300 kDa that are consistently hydrolysed by anti-FVIII IgG, were scanned so as to allow for the calculation of the % of hydrolysis of labelled Factor VII.

The proteolysis of radiolabelled Factor VIII by the anti-Factor VIII allo-antibodies of patient Wal was inhibited to about 62% when the antibodies and Factor VIII were co-incubated in the presence of Pefabloc®, indicating the potency of some serine protease inhibitor to neutralise the catalytic activity of some catalytic antibodies.

Further Observation:

Upon screening the purified IgG of TEN high responder patients with haemophilia A using $^{125}$I-radiolabelled Factor VIII as the target molecule, a change was observed in the migration profile of Factor VIII in the case of six patients. These results substantiate the Applicant's previous observations and indicate that catalytic anti-Factor VIII antibodies are found in about 60% of the patients.

The invention claimed is:

1. A method of determining the presence of anti-Factor VIII allow-antibodies capable of degrading Factor VIII in a mammal, which comprises:
   i) isolating the plasma from a sample of blood taken from said mammal,
   ii) isolating anti-Factor VIII allo-antibodies from said plasma;
   iii) placing said anti-Factor VIII allo-antibodies in contact with Factor VIII for a period of time sufficient to permit any degradation of said Factor VIII by said anti-Factor VIII allo-antibodies; and
   iv) determining, after said period of time, whether said Factor VIII has been degraded by said anti-Factor VIII allo-antibodies.

2. The method of claim 1, wherein in step ii), said anti-Factor VIII allo-antibodies are isolated from said plasma by combining them with said Factor VIII.

3. The method of claim 2, wherein said Factor VIII is coupled to a matrix.

4. The method of claim 1, wherein in step ii), said anti-Factor VIII allo-antibodies are isolated by affinity chromatography.

5. The method of claim 4, wherein in step ii), said affinity chromatography comprises the use of Factor Viii covalently coupled to a Sepharose matrix.

6. The method of claim 5, wherein said Sepharose matrix is activated with cyanogens bromide.

7. The method of claim 1, wherein in step iii), said Factor VIII is labeled with a labeling agent.

8. The method of claim 7, wherein said labeling agent is a radio-labelling agent.

9. The method of claim 8, wherein said radio-labelling agent is $^{125}$I.

10. The method of claim 1, wherein in step iii), said Factor VIII is placed in contact with the anti-Factor VIII allo-antibodies for a period of time of between about 0.5 and about 30 hours, at a temperature of about 15 to about 40° C.

11. The method of claim 1, wherein in step iii), said Factor VIII is placed in contact with the anti-Factor VIII allo-antibodies for a period of time of about 10 hours, at a temperature of about 15 to about 40° C.

12. The method of claim 1, wherein in step iii), said Factor VIII is placed in contact with the anti-Factor VIII allo-antibodies for a period of time of between about 0.5 and about 30 hours, at a temperature of 38° C.

13. The method of claim 1, wherein in step iii), said Factor VIII is placed in contact with the anti-Factor VIII allo-antibodies for a period of time of about 10 hours, at a temperature of 38° C.

14. The method of claim 1, wherein step iv) is carried out by a determination comprising a separation technique and a visualization technique.

15. The method of claim 14, wherein said separation technique is selected from the group consisting of gel electrophoresis, and gel filtration.

16. The method of claim 15, wherein said gel electrophoresis is SDS PAGE.

17. The method of claim 15, wherein said gel filtration is fast protein liquid chromatography gel filtration.

18. The method of claim 15, wherein said visualization technique is autoradiography.

19. The method of claim 1, which further comprises:
   v) characterizing the site(s) in said Factor VIII molecule cleaved by said anti-Factor VIII allo-antibodies.

20. The method of claim 19, wherein said characterization is carried out by placing said Factor VIII in contact with said anti-Factor VIII allo-antibodies capable of degrading Factor VIII, separating and then sequencing the fragments of Factor VIII resulting therefrom.

21. The method of claim 20, wherein said separation is carried out using a gel electrophoresis technique.

22. The method of claim 21, wherein said separation is SDS PAGE.

23. The method of claim 20, wherein said sequencing is carried out using an N-terminal sequencing technique.

24. The method of claim 23, wherein said sequencing carried out using an N-terminal sequencing technique is by using an automatic protein microsequencer.

25. The method of claim 20, wherein said sequencing locates scissile bonds between the A1 and A2 domains, on the N-terminus of the A3 domain and within the A3 domain of the Factor VIII molecule.

* * * * *

SEQUENCE LISTING

```
<160> NUMBER OF SEQ ID NOS: 4

<210> SEQ ID NO 1
<211> LENGTH: 7
<212> TYPE: PRT
<213> ORGANISM: Homo sapiens

<400> SEQUENCE: 1

Ser Val Ala Lys Lys His Pro
1               5

<210> SEQ ID NO 2
<211> LENGTH: 7
<212> TYPE: PRT
<213> ORGANISM: Homo sapiens

<400> SEQUENCE: 2

Asp Glu Asp Glu Asn Gln Ser
1               5

<210> SEQ ID NO 3
<211> LENGTH: 7
<212> TYPE: PRT
<213> ORGANISM: Homo sapiens

<400> SEQUENCE: 3

Asp Gln Arg Gln Gly Ala Glu
1               5

<210> SEQ ID NO 4
<211> LENGTH: 2332
<212> TYPE: PRT
<213> ORGANISM: Homo sapiens

<400> SEQUENCE: 4

Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110
```

-continued

```
Glu Tyr Asp Asp Gln Thr Ser Gln Arg Glu Lys Glu Asp Lys Val
        115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525
```

-continued

```
Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Phe Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
```

-continued

```
            945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
            995                 1000                1005
Thr Asn Arg Lys Thr His Ile Asp Gly Pro Ser Leu Leu Ile Glu Asn
        1010                1015                1020
Ser Pro Ser Val Trp Gln Asn Ile Leu Glu Ser Asp Thr Glu Phe Lys
1025                1030                1035                1040
Lys Val Thr Pro Leu Ile His Asp Arg Met Leu Met Asp Lys Asn Ala
                1045                1050                1055
Thr Ala Leu Arg Leu Asn His Met Ser Asn Lys Thr Thr Ser Ser Lys
            1060                1065                1070
Asn Met Glu Met Val Gln Gln Lys Lys Glu Gly Pro Ile Pro Pro Asp
        1075                1080                1085
Ala Gln Asn Pro Asp Met Ser Phe Phe Lys Met Leu Phe Leu Pro Glu
        1090                1095                1100
Ser Ala Arg Trp Ile Gln Arg Thr His Gly Lys Asn Ser Leu Asn Ser
1105                1110                1115                1120
Gly Gln Gly Pro Ser Pro Lys Gln Leu Val Ser Leu Gly Pro Glu Lys
                1125                1130                1135
Ser Val Glu Gly Gln Asn Phe Leu Ser Glu Lys Asn Lys Val Val Val
            1140                1145                1150
Gly Lys Gly Glu Phe Thr Lys Asp Val Gly Leu Lys Glu Met Val Phe
            1155                1160                1165
Pro Ser Ser Arg Asn Leu Phe Leu Thr Asn Leu Asp Asn Leu His Glu
        1170                1175                1180
Asn Asn Thr His Asn Gln Glu Lys Lys Ile Gln Glu Glu Ile Glu Lys
1185                1190                1195                1200
Lys Glu Thr Leu Ile Gln Glu Asn Val Val Leu Pro Gln Ile His Thr
            1205                1210                1215
Val Thr Gly Thr Lys Asn Phe Met Lys Asn Leu Phe Leu Leu Ser Thr
            1220                1225                1230
Arg Gln Asn Val Glu Gly Ser Tyr Asp Gly Ala Tyr Ala Pro Val Leu
        1235                1240                1245
Gln Asp Phe Arg Ser Leu Asn Asp Ser Thr Asn Arg Thr Lys Lys His
    1250                1255                1260
Thr Ala His Phe Ser Lys Lys Gly Glu Glu Glu Asn Leu Glu Gly Leu
1265                1270                1275                1280
Gly Asn Gln Thr Lys Gln Ile Val Glu Lys Tyr Ala Cys Thr Thr Arg
            1285                1290                1295
Ile Ser Pro Asn Thr Ser Gln Gln Asn Phe Val Thr Gln Arg Ser Lys
        1300                1305                1310
Arg Ala Leu Lys Gln Phe Arg Leu Pro Leu Glu Glu Thr Glu Leu Glu
        1315                1320                1325
Lys Arg Ile Ile Val Asp Asp Thr Ser Thr Gln Trp Ser Lys Asn Met
        1330                1335                1340
Lys His Leu Thr Pro Ser Thr Leu Thr Gln Ile Asp Tyr Asn Glu Lys
1345                1350                1355                1360
Glu Lys Gly Ala Ile Thr Gln Ser Pro Leu Ser Asp Cys Leu Thr Arg
        1365                1370                1375
```

Ser His Ser Ile Pro Gln Ala Asn Arg Ser Pro Leu Pro Ile Ala Lys
        1380                1385                1390

Val Ser Ser Phe Pro Ser Ile Arg Pro Ile Tyr Leu Thr Arg Val Leu
    1395                1400                1405

Phe Gln Asp Asn Ser Ser His Leu Pro Ala Ala Ser Tyr Arg Lys Lys
1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
        1460                1465                1470

Lys Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys Asp
    1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
    1555                1560                1565

Asn His Tyr Gly Thr Gln Ile Pro Lys Glu Glu Trp Lys Ser Gln Glu
    1570                1575                1580

Lys Ser Pro Glu Lys Thr Ala Phe Lys Lys Lys Asp Thr Ile Leu Ser
1585                1590                1595                1600

Leu Asn Ala Cys Glu Ser Asn His Ala Ile Ala Ala Ile Asn Glu Gly
            1605                1610                1615

Gln Asn Lys Pro Glu Ile Glu Val Thr Trp Ala Lys Gln Gly Arg Thr
        1620                1625                1630

Glu Arg Leu Cys Ser Gln Asn Pro Pro Val Leu Lys Arg His Gln Arg
    1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
            1685                1690                1695

His Tyr Phe Ile Ala Ala Val Glu Arg Leu Trp Asp Tyr Gly Met Ser
        1700                1705                1710

Ser Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
        1780                1785                1790

```
Glu Glu Asp Gln Arg Gln Gly Ala Glu Pro Arg Lys Asn Phe Val Lys
        1795                1800                1805

Pro Asn Glu Thr Lys Thr Tyr Phe Trp Lys Val Gln His His Met Ala
    1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
        1860                1865                1870

Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
        1940                1945                1950

Ile His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
        2020                2025                2030

Arg Asp Phe Gln Ile Thr Ala Ser Gly Gln Tyr Gly Gln Trp Ala Pro
        2035                2040                2045

Lys Leu Ala Arg Leu His Tyr Ser Gly Ser Ile Asn Ala Trp Ser Thr
    2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
        2100                2105                2110

Gln Thr Tyr Arg Gly Asn Ser Thr Gly Thr Leu Met Val Phe Phe Gly
    2115                2120                2125

Asn Val Asp Ser Ser Gly Ile Lys His Asn Ile Phe Asn Pro Pro Ile
    2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
        2180                2185                2190

Ser Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val Asn
```

-continued

```
                    2210                2215                2220
Asn Pro Lys Glu Trp Leu Gln Val Asp Phe Gln Lys Thr Met Lys Val
2225                2230                2235                2240
Thr Gly Val Thr Thr Gln Gly Val Lys Ser Leu Leu Thr Ser Met Tyr
                    2245                2250                2255
Val Lys Glu Phe Leu Ile Ser Ser Ser Gln Asp Gly His Gln Trp Thr
                    2260                2265                2270
Leu Phe Phe Gln Asn Gly Lys Val Lys Val Phe Gln Gly Asn Gln Asp
            2275                2280                2285
Ser Phe Thr Pro Val Val Asn Ser Leu Asp Pro Pro Leu Leu Thr Arg
    2290                2295                2300
Tyr Leu Arg Ile His Pro Gln Ser Trp Val His Gln Ile Ala Leu Arg
2305                2310                2315                2320
Met Glu Val Leu Gly Cys Glu Ala Gln Asp Leu Tyr
                    2325                2330
```